United States Patent
Van Den Berghe et al.

(10) Patent No.: US 11,920,247 B2
(45) Date of Patent: Mar. 5, 2024

(54) OXYGEN-GENERATING BIOELECTRICAL REACTOR

(71) Applicant: UNIVERSITY OF SOUTHERN CALIFORNIA, Los Angeles, CA (US)

(72) Inventors: Martin Van Den Berghe, St. John's (CA); Kenneth H. Nealson, South Pasadena, CA (US); A. Joshua West, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 4 days.

(21) Appl. No.: 17/481,545

(22) Filed: Sep. 22, 2021

(65) Prior Publication Data
US 2022/0098739 A1  Mar. 31, 2022

Related U.S. Application Data

(60) Provisional application No. 63/083,686, filed on Sep. 25, 2020.

(51) Int. Cl.
| | |
|---|---|
| C25B 1/00 | (2021.01) |
| C12M 1/00 | (2006.01) |
| C12M 1/107 | (2006.01) |
| C12M 1/42 | (2006.01) |
| C25B 1/04 | (2021.01) |
| C25B 1/50 | (2021.01) |
| C25B 3/25 | (2021.01) |
| C25B 9/19 | (2021.01) |

(52) U.S. Cl.
CPC ............... *C25B 1/50* (2021.01); *C12M 21/04* (2013.01); *C12M 23/34* (2013.01); *C12M 35/02* (2013.01); *C25B 1/04* (2013.01); *C25B 3/25* (2021.01); *C25B 9/19* (2021.01)

(58) Field of Classification Search
CPC .... C25B 1/50; C25B 3/25; C25B 9/19; C25B 1/04; C12M 21/04; C12M 23/34; C12M 35/02
See application file for complete search history.

(56) References Cited

U.S. PATENT DOCUMENTS

| | | | | |
|---|---|---|---|---|
| 2005/0095466 A1* | 5/2005 | Minteer | ............... | H01M 8/16 429/526 |
| 2010/0040908 A1* | 2/2010 | Nealson | ............... | H01M 8/16 429/2 |
| 2015/0259669 A1* | 9/2015 | May | ............... | C12P 7/54 435/252.4 |
| 2019/0203368 A1* | 7/2019 | Cam | ............... | C02F 1/488 |

* cited by examiner

*Primary Examiner* — Zulmariam Mendez
(74) *Attorney, Agent, or Firm* — SNELL & WILMER LLP

(57) ABSTRACT

In various embodiments of the present disclosure, an oxygen-generating bioelectrical reactor comprises two chambers, a first oxidative chamber configured for the abiotic oxidation of water to generate molecular oxygen, and a second reductive chamber configured for the biotic reduction of an insoluble metal(loid) oxide or hydroxide. In various embodiments, the biotic reduction comprises microbially-catalyzed metal(loid) ion reduction of the insoluble metal(loid) oxide or hydroxide, wherein a dissimilatory metal(loid) reducing microorganism transfers electrons obtained from the oxidation of the water extracellularly to the metal(loid) ions.

20 Claims, 6 Drawing Sheets

OXYGEN-GENERATING BIOELECTRICAL REACTOR

CROSS-REFERENCE TO RELATED APPLICATIONS

This application claims priority to, and the benefit of, U.S. Provisional Patent Application Ser. No. 63/083,686 filed Sep. 25, 2020 and entitled "Oxygen-Generating Bioelectrical Reactor." The '686 disclosure is incorporated herein by reference in its entirety for all purposes.

FIELD

The present disclosure generally relates to electrochemical oxygen generators, and in particular to oxygen generating bioelectrical systems based on microbial respiration.

BACKGROUND

Devices capable of generating molecular oxygen $O_2$ and dissolving minerals are useful to many industries, including medicine, scientific research and environmental remediation. But beyond the need for oxygen generators on earth, oxygen generators will be of need for interstellar travel and to sustain life on other planets, such as Mars. Logistical and time constraints inherent to interplanetary travel render any human visit to Mars a deeply committing and isolating enterprise, punctuated at best by very sporadic resupply events. The rapid development of self-sufficiency is therefore critical to any human presence, and is highly dependent on in situ resource utilization (ISRU) systems. Oxygen will be one of the most fundamental necessities for human presence on Mars and elsewhere, to both sustain human life and provide a propellant for spacecrafts.

One experimental oxygen-generating ISRU technology, the Mars oxygen ISRU experiment, or MOXIE, makes use of atmospheric carbon dioxide to generate oxygen gas. This process has very high energy requirements and produces large amounts of carbon monoxide as a by-product, (see for example, F. E. Meyen, et al., "Thermodynamic model of Mars Oxygen ISRU Experiment (MOXIE)," *Acta Astronaut.* 129 (2016) 82-87, (see http://doi.org/10.1016/j.actaastro.2016.06.005). The constraints of this process may make it impractical to support human crews during space travel and human civilizations on other planets.

Oxygen is present on Mars, but it is trapped within metal oxides globally distributed in Martian topsoil. These oxides are generally characterized as poorly crystalline nanophase ferric minerals, including hematite, maghemite, magnetite, goethite, jarosite and schwertmannite. Further, large, coarsely crystalline hematite deposits and spherules have also been found exposed in a number of surficial, water-altered bedrock formations across the planet, with hematite accounting for up to 45 vol. % of some outcrops. These mineral phases contain an abundance of oxygen which, if liberated and transformed, could provide an almost limitless source of $O_2$.

Developments in the past several decades demonstrate the capability of bacteria to conduct extracellular electron transport (EET). EET enables bacteria to fuel their metabolism by transferring electrons across cell membranes to extracellular substrates, including highly insoluble minerals such as iron or manganese oxides. EET-driven metal oxide reductive dissolution implies the congruent release of oxygen from the crystal lattice. The fate of this oxygen after mineral dissolution still remains unknown. Most EET-dependent bioelectric reactors have been developed using anodes as the terminal electron acceptor and soluble organic carbon as the electron donor. Nevertheless, some bacteria are able to use cathodes as electron donors (using oxygen as an electron acceptor), broadening the potential applications in biotechnology and geoengineering.

Although some research investigated microbial biocathode oxidation, the focus has been mainly on the production of hydrogen gas or organic molecules through various reduction processes referred to as microbial electrosynthesis, and not the generation of oxygen. Therefore, there is an ongoing need to develop efficient bioreactors capable of generating oxygen by EET to insoluble minerals such as iron or manganese oxides that may be prevalent on other planets having little to no atmospheric oxygen.

SUMMARY

It has now been surprisingly discovered that oxygen generation is possible from a three-electrode, two-chamber bio-electrochemical reactor that couples the abiotic oxidation of water with microbially-catalyzed metal(loid) ion reduction and dissolution. It is believed that the microbial coupling of two insoluble substrates, namely cathode oxidation and insoluble metal or metalloid ion reduction, has not been described previously.

In various embodiments, an oxygen-generating bioelectrical reactor herein comprises two chambers, namely an abiotic chamber configured for oxidation of water and a biotic chamber configured for insoluble metal(loid) ion reduction and dissolution.

In various embodiments, an oxygen-generating bioelectrical reactor herein comprises a proton-selective membrane separating an oxidative abiotic chamber containing only water from a reductive biotic chamber. The proton-selective membrane operatively couples cathodic oxidation of water with microbially-catalyzed metal or metalloid ion reduction.

In various embodiments, the microbially-catalyzed metal (loid) ion reduction in the biotic chamber comprises anaerobic respiration of the microbes using the metal(loid) ion as the electron acceptor.

In various embodiments, an oxygen-generating bioelectrical reactor herein comprises two chambers, a first chamber in which the half reaction $H_2O=\frac{1}{2}O_2+2e^-+2H^+$ occurs under abiotic oxidative conditions, and a second biotic chamber coupled thereto, in which a microbially-catalyzed reduction of an insoluble metal(loid) oxide or hydroxide occurs under biotic reductive conditions, characterized by the partial half reaction $zM(x)_{(s)}+ze^-=zM(y)_{(aq)}$, wherein x=6, 5, 4, 3, or 2, y=5, 4, 3, 2, or 1, and z is independently 1 or 2.

In various embodiments, an oxygen-generating bioelectrical reactor herein comprises two chambers coupled by a proton-selective membrane, a first chamber comprising a cathode and conditions for cathodic oxidation of water, and a second chamber comprising both a working electrode and a reference electrode and conditions for microbially-catalyzed metal(loid) ion reduction.

In various embodiments of the present disclosure, an oxygen-generating bioelectrical reactor is described. The reactor comprises: a first abiotic oxidative chamber containing water; a second biotic reductive chamber containing an aqueous mixture of dissimilatory metal(loid)-reducing microorganisms and a water-insoluble metal(loid) oxide or hydroxide capable of microbially-catalyzed reduction by the dissimilatory metal(loid)-reducing microorganisms; a proton-selective membrane disposed between the first abiotic oxidative chamber and the second biotic reductive chamber providing a pathway for protons to move from the abiotic oxidative chamber to the biotic reductive chamber; a counter electrode configured in the first abiotic oxidative chamber in contact with the water; a working electrode and a reference electrode configured in the second biotic reductive chamber in contact with the aqueous mixture; and a circuit electrically connecting the counter electrode, working electrode, and reference electrode such that the counter electrode is connected to the working electrode providing a pathway for electrons to move from the abiotic oxidative chamber to the biotic reductive chamber, wherein the circuit is configured to apply an electrical potential between the working electrode and the reference electrode.

In various embodiments, the water-insoluble metal(loid) oxide or hydroxide capable of microbially-catalyzed reduction by the dissimilatory metal(loid)-reducing microorganisms is characterized as comprising metal(loid) ions M(x), wherein M is Fe, Mn, Cr, Mo, V, As, Co, Au, Pd, or Hg, and x=VI, V, IV, III, or II.

In various embodiments, the dissimilatory metal(loid)-reducing microorganisms comprise *Shewanella* or facultative anaerobes.

In various embodiments, the dissimilatory metal(loid)-reducing microorganisms belong to a genus selected from the group consisting of *Clostridium, Aeromonas, Albidiferax, Shewanella, Geobacter, Geothrix fermentans, Deferribacter, Rhondoferax, Desulfobulbus*, or *Thermoanaerobacter*.

In various embodiments, the water-insoluble metal(loid) oxide or hydroxide comprises one of $Fe_2O_3$, $Fe(OH)_3$ or $MnO_2$.

In various embodiments, the circuit comprises a potentiostat.

In various embodiments, the reactor further comprises an electron shuttle in the aqueous mixture of the biotic reductive chamber.

In various embodiments, the electron shuttle comprises at least one of FADH, menadione (1,2,3,4-tetrahydro-2-methyl-1,4-dioxo-2-naphthalene sulfonic acid), lawsone (2-hydroxy-1,4-naphthoquinone), AQ2S (anthraquinone-2-sulfonate), and AQDS (anthraquinone-2,6-disulfonate).

In various embodiments, the potential applied between the working and reference electrodes is from about −300 mV to about −400 mV vs. SHE.

In various embodiments, the water-insoluble metal(loid) oxide or hydroxide comprises $Fe_2O_3$, and the dissimilatory metal(loid)-reducing microorganisms comprise a wildtype or mutant strain belonging to the genus *Shewanella*.

In various embodiments, a method of generating oxygen from water is described. The method comprises coupling oxidation of the water with a microbially-catalyzed reduction of a water-insoluble metal(loid) oxide or hydroxide to generate the oxygen in an oxygen-generating bioelectrical reactor comprising: a first abiotic oxidative chamber containing the water undergoing oxidation; a second biotic reductive chamber containing an aqueous mixture of dissimilatory metal(loid)-reducing microorganisms and the water-insoluble metal(loid) oxide or hydroxide undergoing microbially-catalyzed reduction by the dissimilatory metal(loid)-reducing microorganisms; a proton-selective membrane disposed between the first abiotic oxidative chamber and the second biotic reductive chamber providing a pathway for movement of protons generated from the oxidation of the water from the abiotic oxidative chamber to the biotic reductive chamber; a counter electrode configured in the first abiotic oxidative chamber in contact with the water; a working electrode and a reference electrode configured in the second biotic reductive chamber in contact with the aqueous mixture; a circuit electrically connecting the counter electrode, the working electrode, and the reference electrode, the circuit facilitating movement of electrons generated in the oxidation of the water from the abiotic oxidative chamber through the counter electrode and to the biotic reductive chamber through the working electrode; and an electrical potential applied at a target level between the working electrode and the reference electrode via the circuit; wherein the dissimilatory metal(loid)-reducing microorganisms undergo anaerobic respiration characterized by extracellular electron transfer of the electrons thus obtained from the oxidation of the water to the water-insoluble metal(loid) oxide or hydroxide, and wherein the oxygen is generated within the abiotic oxidative chamber.

In various embodiments, the oxidation of the water in the abiotic oxidative chamber is characterized by the half-cell reaction, $H_2O = \frac{1}{2}O_2 + 2e^- + 2H^+$.

In various embodiments, the microbially-catalyzed reduction of the water-insoluble metal(loid) oxide or hydroxide is characterized by the half-cell reaction, $M(x) \rightarrow M(y)$, wherein M is Fe, Mn, Cr, Mo, V, As, Co, Au, Pd, or Hg, x=VI, V, IV, III, or II, and y=V, IV, III, II or I.

In various embodiments, the target level of the electrical potential thus applied is determined by cyclic voltammetry using the circuit.

In various embodiments, the extracellular electron transfer by the dissimilatory metal(loid)-reducing microorganisms is facilitated by an electron shuttle present in the aqueous solution.

In various embodiments, the electron shuttle comprises at least one of FADH, menadione (1,2,3,4-tetrahydro-2-methyl-1,4-dioxo-2-naphthalene sulfonic acid), lawsone (2-hydroxy-1,4-naphthoquinone), AQ2S (anthraquinone-2-sulfonate), and AQDS (anthraquinone-2,6-disulfonate).

In various embodiments, the electrical potential thus applied between the working and reference electrodes is from about −300 mV to about −400 mV vs. SHE.

In various embodiments, the dissimilatory metal(loid)-reducing microorganisms comprise *Shewanella* or facultative anaerobes.

In various embodiments, the dissimilatory metal(loid)-reducing microorganisms belong to a genus selected from the group consisting of *Clostridium, Aeromonas, Albidiferax, Shewanella, Geobacter, Geothrix fermentans, Deferribacter, Rhondoferax, Desulfobulbus*, or *Thermoanaerobacter*.

In various embodiments, the water-insoluble metal(loid) oxide or hydroxide comprises one of $Fe_2O_3$, $Fe(OH)_3$ or $MnO_2$.

BRIEF DESCRIPTION OF THE DRAWING FIGURES

The subject matter is pointed out with particularity and claimed distinctly in the concluding portion of the specification. A more complete understanding, however, may best be obtained by referring to the detailed description and claims when considered in connection with the following drawing figures:

DETAILED DESCRIPTION

Figure 1:
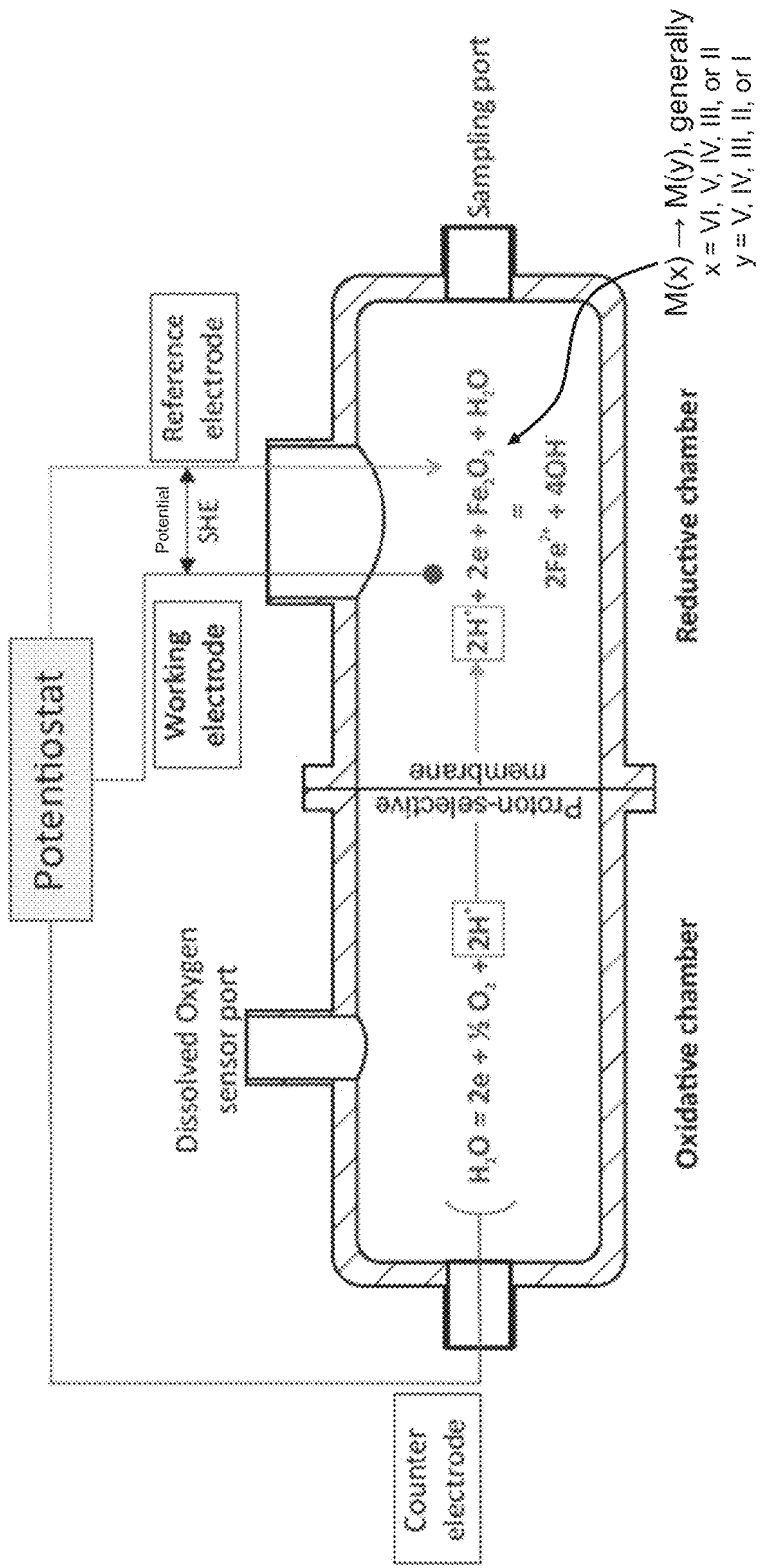
FIG. 1 illustrates a two chamber bio-electrochemical reactor in accordance with various embodiments of the present disclosure, configured to produce molecular oxygen.

The detailed description of exemplary embodiments makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments of the present disclosure, an oxygen-generating bioelectrical reactor is described. The oxygen-generating bioelectrical reactor comprises two chambers, a first oxidative chamber configured for abiotic oxidation of water to oxygen, and a second reductive chamber configured for biotic reduction of an insoluble metal (loid) oxide or hydroxide. In various embodiments, the biotic reduction comprises microbially-catalyzed metal (loid) ion reduction further comprising at least one dissimilatory metal(loid) reducing microorganism. In various embodiments, the first oxidative chamber includes a single counter electrode, and the reductive chamber includes both a working electrode and a reference electrode. In various embodiments, the three electrodes are connected into a circuit by a potentiostat that allows for both a setting of a fixed potential between working and reference electrodes, along with providing a pathway for electrons to move between chambers. In various embodiments, a proton-selective membrane separates the two chambers and provides a pathway for protons. The reactor as thus described produces oxygen in the oxidative chamber, detected as dissolved oxygen in the water within the first oxidative chamber. In various embodiments, the oxygen thus produced is removed from the water such as in vacuo.

Definitions and Interpretations

As used herein, the term "insoluble metal(loid) oxide" or "insoluble metal(loid) hydroxide" refers to water-insoluble ionic metal or metalloid species capable of being reduced by a dissimilatory metal(loid)-reducing microorganism into water-soluble ionic species. Stated another way, an "insoluble metal oxide" or an "insoluble metal hydroxide" are water-insoluble inorganic metal or metalloid species that contain metal(loid) ions $M(x)$ capable of being reduced by microbes into water-soluble inorganic species containing metal(loid) ions $M(y)$. In general, these beginning insoluble minerals containing $M(x)$ include, but are not limited to, the oxides and hydroxides of Fe(III) and Mn(IV), and also the oxides and hydroxides of Cr(VI), Mo(VI), V(V), As(V), Co(III), Au(III), Pd(II), and Hg(II). Since most metal(loid) oxides and hydroxides are water-insoluble, other metal oxide or hydroxide species can be envisioned beyond this brief listing. In various embodiments, the reduction of $M(x) \rightarrow M(y)$ comprises those reductions wherein $x=6, 5, 4, 3$, or 2, and $y=5, 4, 3, 2$, or 1, respectively. That is, $x>y$, the difference between x and y depending on how many electrons e− are involved in the reduction of $M(x)$ to $M(y)$, e.g., one or two e−. In various embodiments herein, the mineral containing $M(x)$ ions is water-insoluble, whereas the reduced substance containing the $M(y)$ ions is water-soluble. Herein, the reduction of $M(x) \rightarrow M(y)$ is microbially-catalyzed, and is characterized by anaerobic respiration of the microbe. That is, the metal(loid) ion $M(x)$ is the terminal electron acceptor for the microbes, rather than molecular oxygen being the electron acceptor as per aerobic respiration. A non-limiting example herein taking place in an oxygen-generating bioelectrical reactor of the present disclosure is the microbially-catalyzed anaerobic reduction of Fe(III) (ferric, $Fe^{3+}$, x=3) ions to Fe(II) (ferrous, $Fe^{+2}$, y=2) ions, wherein the beginning Fe(III) metal species comprises a water-insoluble iron oxide such as hematite. In various embodiments, an insoluble metal(loid) oxide or hydroxide for use herein may be processed as necessary to obtain a desired property, such as a particular particle size distribution or some other physical characteristic. For example, minerals may be crushed to particle sizes in the micrometer or nanometer scale, and minerals may be sterilized prior to combining with microorganisms. Throughout the present disclosure, the term "metal" is recognized as including various "metalloid" species, seeing that As(V) is formally considered as metalloid. As possible, the notation "metal (loid)" is used throughout, and refers herein to both metal and metalloid species.

As used herein, the term "dissimilatory metal(loid) reducing microorganisms," (DMRMs) or more simply, "reducing microbes," or "microorganisms," or most simply, "microbes," refer to those bacteria and archaea capable of utilizing a water-insoluble mineral particle such as $Fe_2O_3$, $Fe(OH)_3$, or $MnO_2$ as the terminal electron acceptor in anaerobic respiration. Generally, the organisms for use herein, given this requirement, fall into the two families, geobacteraceae and facultative anaerobes. Specific organisms in these families for use in an oxygen-generating bioelectrical generator of the present disclosure include, but are not limited to, *Clostridium, Aeromonas, Albidiferax, Shewanella, Geobacter, Geothrix fermentans, Deferribacter, Rhondoferax, Desulfobulbus*, and *Thermoanaerobacter*. Of particular use herein are bacteria belonging to the genus *Shewanella*, (see, for example, L. Shi, et al., "Extracellular electron transfer mechanisms between microorganisms and minerals," *Nature Reviews Microbiology*, 14 (10): 651-662, (2016)). It is important to note that DMRMs for use herein may be wildtype (WT) organisms or genetically engineered mutants.

General Embodiments

In various embodiments, an oxygen-generating bioelectrical reactor is disclosed comprising a first oxidative chamber and a second reductive chamber. In various embodiments, the first chamber is configured to be abiotic and the second chamber is configured to be biotic.

In various embodiments, an oxygen-generating bioelectrical reactor comprises two chambers separated by a proton-selective membrane such that protons generated in one chamber can move through to the other chamber.

In various embodiments, an oxygen-generating bioelectrical reactor comprises two chambers and three electrodes, wherein a first abiotic oxidative chamber is configured with a counter electrode (cathode) for abiotic oxidation of water, and wherein a second biotic reductive chamber is configured with both a working electrode and a reference electrode for microbially-catalyzed reduction of a water-insoluble metal (loid) oxide or hydroxide.

In various embodiments, the three-electrodes, counter, working and reference, are wired into an electrical circuit with a potentiostat, such that the potential of the working electrode can be maintained at a constant level with respect to the reference electrode in the biotic chamber and current can be measured at the counter electrode in the abiotic oxidative chamber.

FIG. 1 illustrates an embodiment of an oxygen-generating bioelectrical reactor according to the present disclosure and the aforementioned features, showing the oxidative abiotic chamber on the left, the biotic reductive chamber on the right, and a proton-selective membrane separating the two chambers such that protons can move from the oxidative chamber to the reductive chamber. Also illustrated in FIG. 1 are access ports, such as to allow sampling of aqueous solutions in either chamber, or to provide a way to position electrodes and maintain a seal to the environment as indicated. Some notations, particularly the half-cell reaction shown in the reductive chamber involving $Fe_2O_3$, are specific to embodiments using that particular insoluble metal oxide, and as such, should not be interpreted in any way as limiting the reactor to only the reduction of $Fe_2O_3$.

In various embodiments, an oxygen-generating bioelectrical reactor such as per FIG. 1 may be made out of glass or other suitable conductive material. The body of the reactor may be created from one piece of material, such as blown glass, or from two (or more) separate pieces that can be clamped together. A two-piece arrangement allows for clamping a proton-selective membrane between two chambers. Openings in the body of the reactor may be fabricated in later, such as by glass blowing techniques, and these are adapted with various fittings into access ports. The access ports may be sealed by rubber or other resilient elastomeric septa such that needles or wires can be pushed through without compromising a seal between the interior of the reactor and the outside environment that surrounds it. A reactor may be connected to other apparatuses as needed, such as a potentiostat, electrical wiring, a vacuum pump, water lines, crushed mineral feeders, and so forth.

In various embodiments, an oxygen-generating bioelectrical reactor comprises two chambers each having, for example, mL-size volumes up to liter-size volumes. Experimental size reactors (e.g., each chamber having a volume of about 1-100 mL) for proof of concept would be smaller than commercial reactor embodiments that could feature significantly larger chamber volumes (e.g., each chamber having a volume in the range of 10's to 100's of liters or greater).

With continued reference to FIG. 1, an oxygen-generating bioelectrical reactor according to the present disclosure comprises three electrodes. As shown, a counter electrode, optionally referred to as an auxiliary electrode, is positioned in the abiotic oxidative chamber. This electrode, such as in the form of a wire, may be disposed and secured through a septum fitted in an access port to this chamber of the reactor. In various embodiments, the biotic reductive chamber includes both a working electrode and a reference electrode. As indicated, an electrical potential is set between the working electrode and the reference electrode, which is discussed in more detail below.

In various embodiments, the three electrodes are connected through a potentiostat to form a circuit, as exemplified in FIG. 1. This is an arrangement for three-electrode cells when the three electrodes are all in the same electrolyte solution. It is believed that this distribution with three electrodes in a two-chamber reactor comprising a proton-selective membrane separating the chambers is entirely unique. Further, the auxiliary electrode, along with the working electrode, provide the circuit over which current is measured rather than applied. In the circuit configuration shown herein, a known potential is applied, and the current is measured. Cyclic voltammetry, where the working electrode potential is ramped linearly versus time, can be used to characterize the activity in the system, and obtain an optimal value for this potential.

In various embodiments, an auxiliary electrode configured in the abiotic oxidative chamber comprises one or more corrosion resistant materials, such as carbon or one or more relatively inert metals. For example, the auxiliary electrode may comprise any combination of carbon, titanium, platinum, and gold. In various embodiments, an auxiliary electrode for use herein is a metal wire auxiliary electrode, such as a platinum wire auxiliary electrode, or a gold wire auxiliary electrode. In various embodiments, the auxiliary electrode comprises a titanium wire auxiliary electrode coated with platinum. Various metal wire auxiliary electrodes suitable for use in an oxygen-generating bioelectrical reactor according to the present disclosure are available, for example, from BASi Research Products, West Lafayette, IN, or from eDAQ, Inc., Colorado Springs, CO For example, an auxiliary electrode for use herein is the ET078-1 70 mm auxiliary electrode available from eDAQ, Inc. This exemplary electrode comprises a platinum coated titanium wire, measuring 70 mm in length and 1.6 mm in diameter. The auxiliary electrode is disposed within the abiotic oxidative chamber through an access port configured with an elastomeric septum or some other seal, allowing for its connection to the potentiostat while maintaining an environmental seal around its entry point.

In various embodiments, a working electrode configured in the biotic reductive chamber comprises any combination of inert conductive materials such as indium, gold, silver, nickel, gold/mercury amalgam, platinum, glassy carbon, carbon paste, boron-doped diamond, pyrolytic carbon, various oxides, and so forth, optionally on glass. In various embodiments, the working electrode comprises an indium-tin oxide (ITO)-coated conducting glass electrode, which can be made from ITO coated conducting glasses having a sheet resistance of about 8-10Ω (e.g., from Solaronix SA, Auboone, Switzerland). Working electrodes are available, for example, from BASi Research Products, West Lafayette, IN, or SPI supplies, West Chester, PA.

In various embodiments, a reference electrode configured in the biotic reductive chamber comprises a silver/silver chloride (Ag—AgCl) electrode. Silver chloride reference electrodes for use herein include, but are not limited to, Ag/AgCl/saturated KCl, Ag/AgCl/3.5 mol/kg KCl, Ag/AgCl/3.0 mol/kg KCl, Ag/AgCl/1.0 mol/kg KCl, Ag/AgCl/0.6 mol/kg KCl, and Ag/AgCl/seawater. Preferred for use herein is the Ag/AgCl/saturated KCl reference electrode. Such reference electrodes are available, for example, from DEK Research Instrumentation, New South Wales, Burwood, Australia.

The proton-selective membrane illustrated in FIG. 1, also referred to as a proton-exchange membrane, or "PEM," can be any semipermeable substance configured to conduct protons while acting as an electrical insulator (no e– transfer) and acting as a barrier to transfer of gasses such as oxygen. Suitable membranes for use herein are found in fuel cells. The preferred PEMs for use herein are thin, such as from about 0.001 inches to about 0.002 inches in thickness. Representative membranes for use herein are sold under the brand name Nafion™ by FuelCellStore, Inc., College Station, TX Exemplary membranes for use herein to separate the abiotic oxidative chamber from the biotic reductive chamber include Nafion™ 212, Nafion™ 211, and Nafion™ XL, with the latter (the thinnest and also chemically reinforced) being the most preferred. Thicker Nafion™ membranes find use in cell configurations where there is pressure, and may be appropriate for use in an oxygen-generating bioelectrical reactor according to the present disclosure if a vacuum, for example, is applied to a chamber, such as applied to the abiotic oxidative chamber to remove the resulting dissolved oxygen generated therein.

In various embodiments, the electrolyte solution in the abiotic oxidative chamber comprises water. The water may be deionized to an ultrapure state, (Type 1, 18.2 MΩ or milli-Q designation). UV photo oxidation and ultrafiltration can be used, or a reverse osmosis (RO) system to obtain ultrapure water for use herein. With the reactor configured as described, with the microbes, metal oxide or hydroxide, the electrodes and the potentiostat for a circuit, the half-cell reaction occurring in the abiotic oxidative chamber of the reactor is: $H_2O=\frac{1}{2}O_2+2e^-+2H^+$. The oxidative chamber is thus configured with an oxidative and acidic environment, creating molecular oxygen by this reaction. Further, and with the reactor configured as described, the electrons will flow to the working electrode in the biotic reductive chamber of the reactor and the protons thus formed from splitting water will diffuse through the proton-selective membrane and into the biotic reductive chamber. In various embodiments, the oxygen thus formed is the desired end product, and in early phases of production it will appear only as dissolved oxygen (DO) in the water of the abiotic oxidative chamber. As the electrochemical reactions proceed, it is possible that molecular oxygen will form visible bubbles and evolve from the water. In other embodiments, the water having the DO can be removed from the chamber and the oxygen recovered in vacuo, or the abiotic oxidative chamber can be kept under vacuum and the liberated oxygen pulled from the chamber continuously rather than in sampled batches.

In various embodiments, the biotic reductive chamber contains an aqueous mixture. The water used for this aqueous mixture can be ultrapure, or other grade of water, but preferably sterilized water since the reductive chamber will have microorganisms present.

In various embodiments, the biotic reductive chamber further contains a water-insoluble metal(loid) oxide or hydroxide, as defined/described above. This mineral can be previously crushed, milled or ground to particle sizes averaging <100 μm, <75 μm, <50 μm, or <25 μm. In various embodiments, the mineral may comprise nanoparticles. Preferably the mineral is previously sterilized prior to use in the reactor, such as by UV radiation. The amount of mineral depends on the size of the reactor, and may be on the order of milligrams to kilograms. In various embodiments, about 0.01 grams to about 1.0 grams of the water-soluble mineral is used in the reactor. Since the mineral is consumed in the process of generating oxygen, it can be replaced by batch-wise addition or by a continuous process.

In various embodiments, the biotic reductive chamber comprises at least one metal(loid) oxide or hydroxide, wherein the metal(loid) is selected from the group consisting of Fe(III), Mn(IV), Cr(VI), Mo(VI), V(V), As(V), Co(III), Au(III), Pd(II), Hg(II), and mixtures thereof. Mixed metal (loid) oxides and hydroxides, such as might be found in mined ores find use herein, as well as Metal-Organic Frameworks (MOF). MOFs such as Fe-BTC (BTC=1,3,5-benzenetricarboxylate), $Fe_3O(BTC)_2(OH)\cdot nH_2O$ (MIL-100), and $Fe_3O[(C_2H_2(CO_2)_2]_3(OH)\cdot nH_2O$ (MIL-88A) can be used. These materials are useful when naturally occurring metal(loid) oxides or metal(loid) hydroxides are not needed and the synthetic MOB are otherwise available. A MOF necessarily provides more surface area than a naturally occurring mineral.

Preferably the mineral incorporated in the biotic reductive chamber of the reactor comprises iron (III) oxide or manganese (IV) oxide, recognizing that there are many physical forms/polymorphs/phases of these substances, any one of which find use herein. For example, $Fe_2O_3$ for use herein may comprise $\alpha$-$Fe_2O_3$, $\beta$-$Fe_2O_3$, or $\gamma$-$Fe_2O_3$, such as maghemite, or hematite. Further, hydrated oxides that are characterized as hydroxides or "oxide-hydroxide" can also be used. A non-limiting example is iron(III) oxide-hydroxide (or ferric oxyhydroxide, or rust) having the formula FeO (OH). The hydrate of this substance is iron(III) hydroxide, (hydrated iron oxide, or Pigment Yellow 42), which also finds use herein as an insoluble mineral capable of biotic reduction by a DMRM.

In various embodiments, the biotic reductive chamber further comprises at least one dissimilatory metal(loid) reducing microorganism (DMRM) as defined/described above. The organism is able to reduce the metal(loid) oxide or hydroxide present. Any organism capable of microbial respiration on an insoluble mineral finds use herein. Stated another way, organisms useful for the reactor have extracellular electron transport (EET) capability and a reduced oxygen metabolism. Developments in the past several decades have demonstrated the capability of bacteria to conduct EET. EET enables bacteria to fuel their metabolism by transferring electrons across cell membranes to an extracellular substrate, such as described in this disclosure, highly insoluble mineral phases such as iron or manganese oxides or hydroxides. Various organisms for use herein are disclosed, for example, in O. Bretschger, et al., "Current Production and Metal Oxide Reduction by *Shewanella oneidensis* MR-1 Wild Type and Mutants," *Appl. Environ. Microbiol.* 73, 7003-7012, 2007.

In various embodiments, the reaction occurring in the biotic reductive chamber can be generalized as $M(x) \rightarrow M(y)$, wherein x>y, and wherein M is a metal(loid) such as Fe or Mn, and x represents the ionic state. In various embodiments, x=6, 5, 4, 3, or 2, (otherwise denoted as VI, V, IV, III, or II) and y=5, 4, 3, 2, or 1, (otherwise denoted as V, IV, III, II, or I), respectively. In various embodiments herein, the mineral containing M(x) ions is water-insoluble, whereas the reduced substance containing the M(y) ions is water-soluble. In the biotic reductive chamber configured with the DMRM, the reduction of $M(x) \rightarrow M(y)$ is microbially-catalyzed, and is characterized by anaerobic respiration of the DMRM microorganism. Depending on the nature of the metal species M(x) (e.g., $Fe_2O_3$ or other oxide or hydroxide), the balanced half-cell reaction will have various molar amounts of OH and water on either side of the reaction equation. For example, the half-cell reaction in the biotic reductive chamber in the case of $Fe_2O_3$ is, $Fe_2O_3+2e^-+H_2O+2H^+=2Fe^{2+}+4OH^-$, whereas for other oxides and hydroxides, e.g., $MnO_2$, containing Mn(IV) metal, the stoichiometry of this reaction will be different, yet can still be generally represented as $M(x) \rightarrow M(y)$.

In various embodiments, an electron shuttle is provided in the biotic reduction chamber to serve as a transport molecule between the dissimilatory metal(loid) reducing microorganism and the metal(loid) oxide or hydroxide particles.

The electron shuttle may be any quinone- or semiquinone-containing compound, such as a flavonoid. Many exemplary quinone-containing electron shuttle compounds naturally occur in soils and sediments and are utilized by microorganisms in the soils and sediments, and thus find use here. Examples include, but are not limited to, menadione (1,2,3,4-tetrahydro-2-methyl-1,4-dioxo-2-naphthalene sulfonic acid), lawsone (2-hydroxy-1,4-naphthoquinone), AQ2S (anthraquinone-2-sulfonate), and AQDS (anthraquinone-2,6-disulfonate). In various embodiments, the biotic reductive chamber of the oxygen-generating bioelectrical reactor herein comprises AQDS. In various embodiments, FADH, the reduced form of flavin adenine dinucleotide (FAD), finds use herein as an electron shuttle.

For an oxygen-generating bioelectrical reactor such as per FIG. 1 to generate molecular oxygen, the three electrodes, auxiliary, working and reference, are connected as mentioned to a potentiostat to form a circuit. The potentiostat allows an electrical potential to be set between the working and reference electrodes, and provides a pathway for electrons to flow between chambers.

A target electrical potential for setting the potentiostat depends on a number of factors, including the type of insoluble metal(loid) oxide or hydroxide, the nature of the DMRM, and the salinity and pH of the aqueous mixture in the biotic reductive chamber. Nonetheless, the operating potential will be at least 3.5 to 5-times less than a typical potential for electrochemical hydrolysis. In various embodiments, a target potential across the working and reference electrodes is from about −300 mV to about −400 mV versus a standard hydrogen electrode (SHE). This range should not be viewed as limiting, in that combinations of insoluble mineral species and DMRMs (even currently unknown mutant strains yet to be discovered) could require a potential outside of this range.

In any event, an optimal potential at which the working electrode may be set to can be determined by cyclic voltammetry. In this case, one will use the potentiostat to ramp the working electrode potential versus time, and then ramped in the opposite direction to return to the initial potential, in cyclical phases. The potential is measured between the working electrode and the reference electrode, while the current is measured between the working electrode and the counter electrode. The cyclic voltammogram resulting will suggest an optimized potential at which to operate the reactor. In various embodiments, a target potential across the working and reference electrodes may be set to about −300 mV to about −400 mV versus a standard hydrogen electrode (SHE).

EXPERIMENTAL

A two-chambered, three electrode bio-electrochemical reactor resembling the structure and assembly in FIG. 1 was custom-built out of borosilicate glass and rubber septa, and was configured per below for cathodic oxidation of water coupled to microbially-mediated iron reduction. The device as configured per the below description was capable of oxidizing water and generating molecular oxygen as indicated by measurements of dissolved oxygen forming in the abiotic oxidative chamber.

The reactor was built from two borosilicate components, each component providing a chamber, held together by a clamped flange, sealed by a pair of custom-built Viton chemical-resistant rubber sheet O-rings (McMaster-Carr, Santa Fe Springs, CA). Sampling ports and the counter electrode were placed through crimped butyl rubber septa.

The two chambers thus clamped together were separated by a Nafion™ XL proton selective membrane (a PSM), sourced from Fuel Cell Store, College Station, TX The PSM was cleaned and prepared following standard procedures found in K. J. Chae, et al., "Mass Transport through a Proton Exchange Membrane (Nafion) in Microbial Fuel Cells," Energy Fuels, 22, 169-176 (2008), (see https://doi.org/10.1021/ef700308u).

The reductive chamber contained a working electrode made of indium-tin oxide (ITO)-coated glass (~6.5 cm$^2$, SPI supplies, West Chester, PA) and a custom-built reference electrode of Ag—Ag/Cl in saturated KCl solution, both connected to a potentiostat (eDAQ Inc., Colorado Springs, CO), with a working potential set at −351 mV vs. standard hydrogen electrode (SHE). As mentioned, the working potential could be set to between about −300 mV and −400 mV vs. SHE, although in this case, cyclic voltammetry was not used in determining this chosen setting of −351 mV vs. SHE.

To ensure airtight connections, the working and reference electrodes were emplaced in a rubber stopper and sealed with high temperature airtight silicone gasket as well as with high vacuum grease. All apparatuses were confirmed airtight through continuous dissolved oxygen (DO) readings in static tests, confirming DO readings were not affected by atmospheric contamination. All reactor chamber components were sonicated in 10% Liquinox® detergent, acid-washed, and autoclaved prior to use. Electrodes were washed in acetone and 70% ethanol prior to autoclaving and use. DO microsensors were acid washed and sterilized with 70% ethanol prior to use The reductive chamber further contained 0.1 g of crushed (<63 μm particle size), UV-sterilized red ochre hematite (Ward's Science, Rochester, NY). In biotic experiments, this chamber was populated by a Cyo-A gene-deletion mutant strain of Shewanella oneidensis MR-1, chosen for its EET capabilities and reduced oxygen metabolism. In the abiotic control experiments, the microbe was left out of the reductive chamber. The reaction that took place in the reductive chamber was characterized by the following electrochemical reaction: $Fe_2O_{3(s)}+2e^-+H_2O+2H^+=2Fe^{2+}_{(aq)}+4OH^-$, with the electrons being introduced into the reductive chamber by the ITO cathode, creating a reductive and alkaline environment.

The oxidative chamber contained autoclaved 18.2 MΩ·cm water, a 100 μm dissolved oxygen (DO) microsensor (Unisense, Aarhus, Denmark), and a custom-built counter electrode made from titanium and platinum wires (also connected to the potentiostat per FIG. 1). The oxidative chamber provided an oxidative and acidic environment, creating molecular oxygen characterized by the electrochemical reaction: $H_2O=\frac{1}{2}O_2+2e^-+2H^+$. As mentioned, the electrons move through the electrical circuit whereas the protons move across the proton-selective membrane.

Culturing Conditions

Preparing for biotic experiments, a single colony of *Shewanella oneidensis* MR-1 Cyo-A deletion bacterium was grown at 30° C. in an oxygenic, 18 mM lactate minimal medium to an optical density (OD) at 600 nm of ~1.0. See, for example, O. Bretschger, et al., "Current Production and Metal Oxide Reduction by *Shewanella oneidensis* MR-1 Wild Type and Mutants," *Appl. Environ. Microbiol.* 73 (2007) 7003-7012, and O. Bretschger, et al., "Comparative Microbial Fuel Cell Evaluations of *Shewanella* spp.," *Electroanalysis,* 22 (2010) 883-894. To induce a preliminary cell attachment to the working ITO electrode and promote electro-active pathways, 1 mL of this culture was triple-rinsed and injected into a 3-electrode single chamber cell containing the same 18 mM lactate minimal medium, kept anoxic through constant $N_2$ purging and a set potential of 699 mV vs. SHE.

After approx. 24 hours of lactate-oxidizing, anode-reducing growth, the working and reference electrodes were removed from this chamber, rinsed with sterile experimental minimal medium, and introduced into the biotic reductive chamber of the 2-chamber reactor, thus transferring biofilm-attached cells into the experimental reactor. Additionally, a set number of cells were extracted from the high density, aerobic, 18 mM lactate medium growth flask, triple-rinsed in sterile minimal medium, then injected in the biotic chamber of the bio-electrochemical reactor in order to reach the desired experimental densities ($10^7$ and $10^8$ cells/mL). The minimal medium in the biotic chambers was the same as described above, but lacked both a carbon source and a buffer, and had a starting pH of 8. These choices were designed to force cells to use the cathode as an electron donor, promoted cross-PSM proton transfer, and removed a significant proton sink (i.e. the buffer) that could otherwise impact alkalinity gradients.

Anthraquinone-2,6-disulfonate (AQDS, final concentration of 100 μM) and hematite were introduced into the biotic reductive chamber, parts of the latter settling directly onto the biofilm-supporting working electrode. Both chambers of the reactor were then purged with filtered (0.2 μm) $N_2$ gas for up to three hours, with DO readings confirming stable anoxic conditions. The experiments began when initial $N_2$ purging ended, and the cathodic potential was set (−351 mV vs. SHE) on the working electrode. Abiotic experiments were performed by simply introducing autoclaved electrodes into a sterile experimental reactor, bypassing all preparatory cell growth and injection steps, and with both chambers containing 0.3% formaldehyde (from a pH-neutral concentrate). The use of formaldehyde was deemed necessary due to contamination risks previously encountered from the large number of manipulations involved in assembling the experimental apparatus. Purging of the biotic chamber with filtered $N_2$ gas (~40 cc/min) was performed ~20 hours into the experiments as a means of mixing the medium in the biotic chambers, and to test the added effects of increased medium flow across the working electrode and PSM, as AQDS reaction rates are known to be affected by flow rates, and microbial fuel cells have been shown to be rate-limited by proton diffusion across the PSM.

Microscopy and Activity

Samples were extracted from the biotic reductive chamber during experiments, with aliquots separated for total cell count using acridine orange (1 mg/mL stock) to quantify total planktonic cells. Redox sensor green (RSG) stain, prepared as specified by the manufacturer (Molecular Probes, Fisher Scientific, Waltham, MA) was also used to quantify RSG cell counts based on activity of the electron transport chain, both in the planktonic phase (throughout the experiments), and on the working electrodes (at the end of the experiments). Images and counts were performed under a Zeiss Axio optical microscope. Reduced ferrous ion Fe(II) concentrations were measured from duplicate sample aliquots (n=2) of the biotic chamber following an established ferrozine protocol using a FLUOstar Optima (BMG Labtech, Cary, NC) micro plate reader. pH measurements were performed at the end of the experiments using BDH narrow range strips (Prosource Scientific, Ottawa, ON, Canada). The bio-electrochemical activity in the form of electrical current was monitored and recorded at 60 second intervals with the eDAQ potentiostat. DO concentrations were measured every 60 seconds using a microsensor connected to a multichannel amplifier/multimeter (Unisense, Aarhus, Denmark).

SEM secondary electron and EDAX imaging were performed on electrode materials following experiments with a Nova NanoSEM 450 (FEI, Hilsboro, OR) at the Core Center for Excellence in Nano Imaging at USC. Working distances of 5-10 mm and an accelerating voltage of 10 kV were used. All samples were prepared using a 7-step ethanol dehydration process, fixed with a critical point dryer (Tousimis, Rockville, MD), and coated with a Pt/Pd Cressington 108 sputter-coater.

Results

Cathode oxidation-hematite reduction experiments were performed with *S. oneidensis* cells injected in the reductive chamber at concentrations of 0, $10^7$ and $10^8$ cells/mL. The minimal growth medium was notably unbuffered, pH 8, and contained 100 μM anthraquinone-2,6-disulfonate (AQDS) as the electron shuttle, with the abiotic control experiments also containing 0.3% formaldehyde. Oxidative chambers merely contained sterile 18.2 MΩ·cm water (i.e., even in the biotic experiments, the oxidative chamber remained abiotic). All experiments showed stabilized electric current production within the first few hours to 1-4 μA, with biotic experiments showing measurable dissolved oxygen (DO) concentrations (2-5 μM) in the first 20 hours. Current production increased by an order of magnitude (up to 40 μA) in all experiments as soon as mixing of the reductive chamber began, corresponding with increased DO readings (5-25 μM) for the biotic experiments. No DO was recorded in the abiotic experiments. Dissolved iron concentrations increased significantly above background by the end of the experiment with $10^8$ cells/mL.

While the starting pH values were very different in the two chambers of the experiments (growth medium pH=8, 18.2 MΩ·cm water pH=5.2), all experiments showed equal pH values in both chambers by the end of the experiments, with the biotic experiment chambers ending at pH 7.4-7.6, and the abiotic control chambers ending at pH 5.0-5.2. Planktonic cell densities remained constant and close to the intended values, with Redox Sensor Green (RSG) fluorescent cells accounting for 25-50% of total planktonic cell counts in both biotic experiments, confirming that bacteria had active electron transport chains. RSG-staining of the working electrode also showed pervasive colonization of electro-active cells on hematite particles under optical microscope imaging, with a density of ~$10^5$ cells/mm² by the end of the biotic experiments. Scanning electron microscope (SEM) imaging further confirmed working electrodes populated by *S. oneidensis* cells with nanowire-like structures (visible in SEM as rod-shaped objects) connecting ferric oxide minerals (visible in the SEM as sharp-edged light greyish/white objects) and the electrode. These results are consistent with a bio-electrochemical system that supports the coupling of cathode oxidation and iron reduction facilitated by microbial electron transport.

Figure 2A:
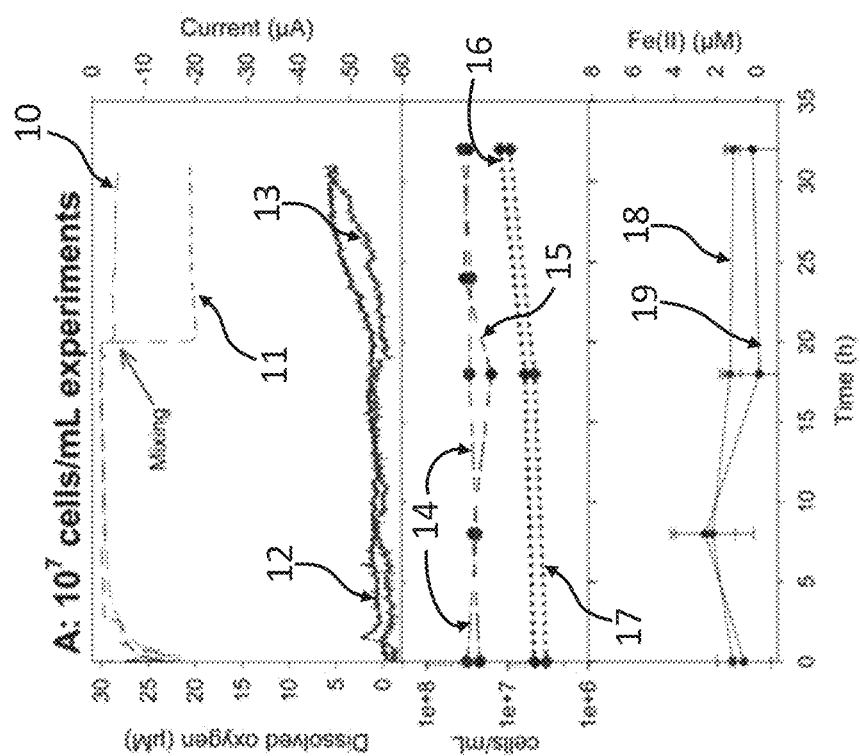
FIG. 2A illustrates dissolved oxygen levels produced by a two chamber bio-electrochemical reactor containing $10^7$ *S. oneidensis* cells/mL.
Figure 2B:
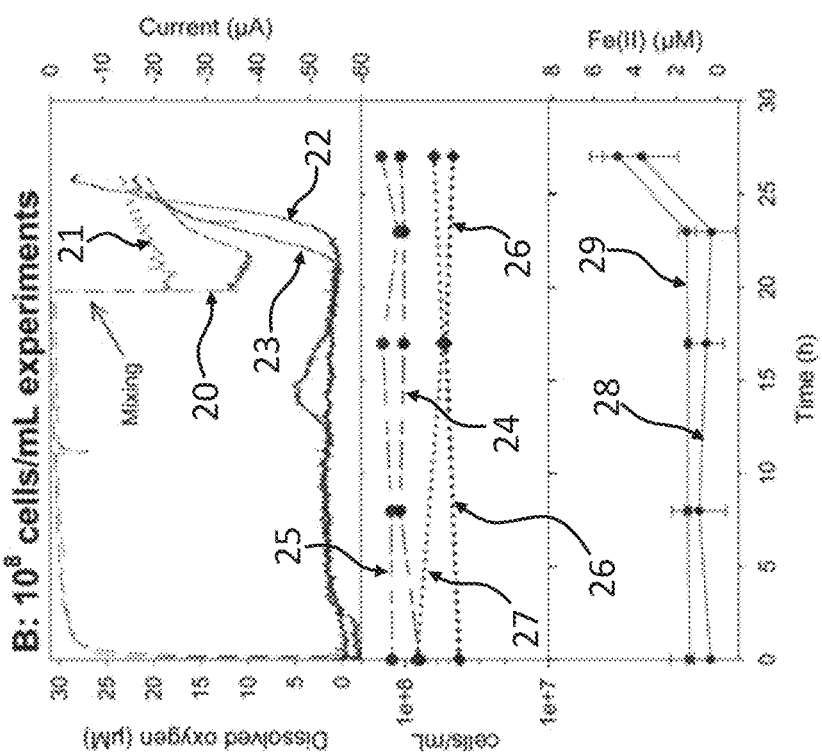
FIG. 2B illustrates dissolved oxygen levels produced by a two chamber bio-electrochemical reactor containing $10^8$ *S. oneidensis* cells/mL.
Figure 2C:
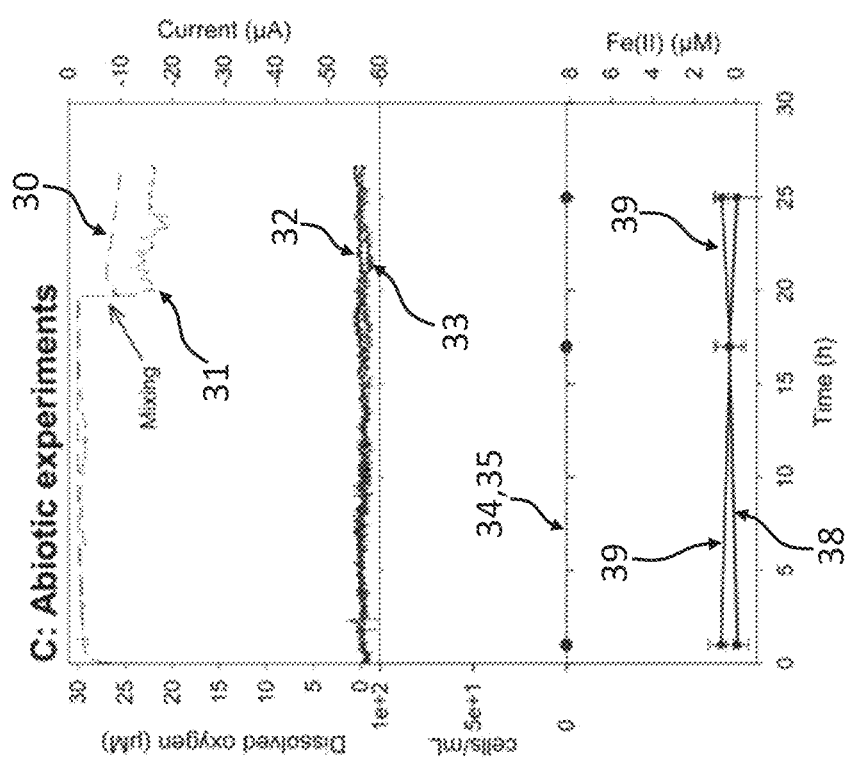
FIG. 2C illustrates experimental results observed for a two chamber bio-electrochemical reactor running under abiotic conditions.

FIGS. 2A, 2B and 2C show these results graphically, with FIG. 2A showing the results when the reactor is charged with $10^7$ S. oneidensis cells/mL, FIG. 2B showing the results when the reactor is charged with $10^8$ S. oneidensis cells/mL, and FIG. 2C showing the abiotic experimental results (when there are no organisms in the reductive chamber to engage in EET). The upper part of each graph shows both the dissolved oxygen readings (µM) and the electrical current readings (µA) over time, with marked changes occurring at mixing of the reductive chamber as mentioned above. The middle portion of each graph shows the microbial counts (cells/mL), recognizing that in the abiotic experiment (FIG. 2C) there are no microbial counts, and the lower portion of each graph shows the ferrous Fe(II) levels (µM), over time. Cell counts in FIGS. 2A and 2B include both RSG cells and total cells. As indicated, each graph represents the results from duplicate experiments, as indicated below with reference numerals on the plots.

With reference now to FIG. 2A, a biotic experiment with $10^7$ S. oneidensis cells/mL in the biotic reductive chamber resulted in the electric current profile 10 for duplicate 1 and current profile 11 for duplicate 2. Current production increased, as mentioned, at the time of mixing (note the graph for current (µA) increases in negative amperage from top to bottom along the y-axis). DO is indicated by the reading 12 (duplicate 1) and reading 13 (duplicate 2). The dashed lines 14 and 15 represent the total cell count in duplicates 1 and 2, respectively. The dotted lines 16 and 17 represent the RSG cell counts for duplicates 1 and 2, respectively. Lastly, the solid line plots 18 and 19 represent the ferrous Fe(II) concentrations over time for duplicates 1 and 2, respectively.

With reference now to FIG. 2B, a biotic experiment with $10^8$ S. oneidensis cells/mL in the biotic reductive chamber resulted in the electric current profile 20 for duplicate 1 and current profile 21 for duplicate 2. Current production increased, as mentioned, at the time of mixing (note the graph for current (µA) increases in negative amperage from top to bottom along the y-axis). DO is indicated by the reading 22 (duplicate 1) and reading 23 (duplicate 2). The dashed lines 24 and 25 represent the total cell count in duplicates 1 and 2, respectively. The dotted lines 26 and 27 represent the RSG cell counts for duplicates 1 and 2, respectively. Lastly, the solid line plots 28 and 29 represent the ferrous Fe(II) concentrations over time for duplicates 1 and 2, respectively.

As mentioned, both DO and dissolved iron Fe(II) concentrations increased significantly above background by the end of the experiment with $10^8$ cells/mL as compared to the biotic experiment with $10^7$ cells/mL.

With reference now to FIG. 2C, an abiotic experiment with no S. oneidensis cells or any microorganisms of any kind in the biotic reductive chamber resulted in the electric current profile 30 for duplicate 1 and current profile 31 for duplicate 2. Current production increased, as mentioned, at the time of mixing (note the graph for current (µA) increases in negative amperage from top to bottom along the y-axis). DO is indicated by the reading 32 (duplicate 1) and reading 33 (duplicate 2), which was essentially none, the expected result when no organisms are present to promote EET. The flat lines 34 and 35 confirm there were no microorganisms present and that the reductive chamber remained abiotic. Lastly, the solid line plots 38 and 39 represent the ferrous Fe(II) concentrations over time for duplicates 1 and 2, respectively

DISCUSSION

Together, the results highlight a novel non-photosynthetic oxygen production pathway catalyzed by the microbial transfer of electrons from a cathode to ferric oxide minerals. Cell density seems to play an important role in the magnitude of electric current production, and more importantly, strongly affects the amount of DO production. Keeping a well-mixed biotic chamber significantly increased both current and DO production. This is likely due to increased medium flow across the working electrode and the proton selective membrane (PSM), as AQDS reaction rates are known to be affected by flow rates, and proton diffusion rates across a PSM can impact electrical current generation. Mixing also likely increased the reactivity of the hematite particles by increasing their surface area exposure to a flowing medium, consistent with a measurable increase in dissolved iron concentrations in the higher cell density experiment after mixing.

Interestingly, the abiotic control experiments also showed current production on a similar scale to the biotic experiments, though no DO was measured. The current observed is attributed to abiotic electrochemical reduction of AQDS, coupled with oxidation of formaldehyde that was inserted in the abiotic controls. Formaldehyde oxidation is a known acidity-producing reaction, and this process would be consistent with the notably lower pH at the end of the abiotic controls (5.0-5.2) than at the end of the biotic experiments (7.4-7.6).

Overall, the two-chamber biochemical reactor separates microbially-catalyzed reductive and oxidative reactions, providing mechanistic insight into oxidative pathways for anaerobic environments. With iron oxide reduction generating significant alkalinity, iron reduction in the reductive chamber would strongly promote the transfer of protons from the oxidative moiety across the PSM. This process, along with the established electric potential from the electrodes, would combine strong electric and alkalinity gradients, and drive an oxygen-generating reaction from water. Significantly, generating molecular $O_2$ would not be strictly required to create a strong oxidative pressure: the same cathode oxidation-hematite reduction experiments made in a single-chamber apparatus generated no detectable oxygen, but created significant manganese and iron oxide precipitation on the counter electrode.

Combined, these reactions in the experimental bioreactor created gradients in electric potential as well as alkalinity across the two chambers of the bioreactor. While mixing the reductive chambers increased both electric current and oxygen production, the magnitude of oxygen production is a function of cell density. This suggests that the presence of electro-active cells is critical in generating oxygen. This system promoted molecular oxygen production through a stepped reaction, whereby microbially-catalyzed iron reduction through cathode oxidation was balanced by the oxidation of water at the counter electrode. The PSM allowed the diffusion of free protons while blocking the flow of reactants and microbes between chambers.

Using bio-electrochemical reactors offers significant advantages, as they could be powered directly by solar energy, removing the need for consumable organic electron donor substrates. They also provide a charge-balancing oxidant in the counter electrode, providing the critical step in oxidizing reduced oxygen species and ensuring molecular oxygen production. In this context, EET-capable bacteria can act as an effective catalyst for the reductive dissolution of ferric oxide and other minerals and corresponding molecular oxygen production.

Active Bacterial EET

Figure 3:
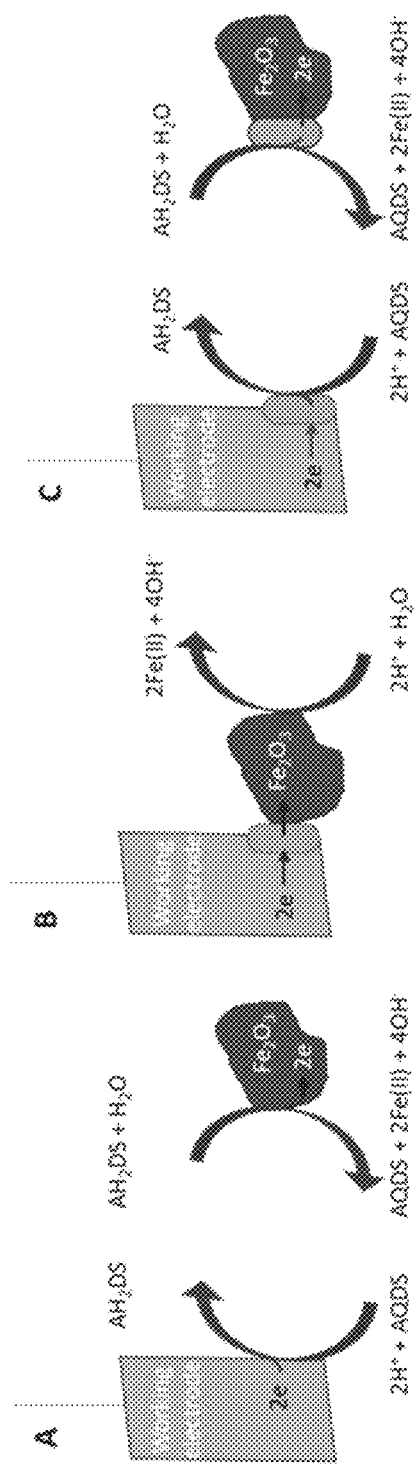
FIG. 3 illustrates possible pathways for electron transfer from the working electrode to $Fe_2O_3$ in a two chamber bio-electrochemical reactor.

FIG. 3 sets forth three (A, B, C) proposed pathways for electrons to flow from the working electrode to the ferric oxide particles, in oxygen-generating bioelectrical reactors in accordance with the present disclosure. Part (A) of FIG. 3 shows abiotic electrochemical transfer through AQDS shuttles, which may occur in both the biotic and abiotic experiments but which appears to be limited based on the minimal observed dissolved $O_2$ production in the abiotic experiments conducted herein. Part (B) of FIG. 3 shows direct microbial solid-to-solid electron transfer. Part (C) of FIG. 3 shows indirect solid-to-solid electron transfer via AQDS (or other) electron shuttles, which appears to be the most likely candidate for DO production in the biotic experiments conducted herein, given the addition of the electron shuttle molecule.

The congruent AQDS redox reactions and ferric oxide dissolution likely impact proton activity. These effects would promote the flow of protons across the PSM to maintain mass and charge balance between the two chambers, leading to oxygen production by driving the proposed water splitting in the oxidative chamber. The putative metabolic mechanism driving these reactions would involve the previously reported reversal of electron flow through the respiratory pathway involving an Mtr gene. While it has been suggested that bacterial cathode oxidation offers scant metabolic energy and thus supports only limited growth rates, mere bacterial maintenance, survival, or even presence may be enough to catalyze the key oxidizing geochemical reactions. Abiotic controls on the other hand have fewer pathways to transfer electrons, and associated proton flux, thus limiting reaction rates and oxygen production.

ISRU Systems

The bio-electrochemical reactor used in the experiments presented herein were static, batch reactors with no water or medium inflows or outflows, and the experiments contained finite amounts of consumable ferric oxide minerals. Such a configuration is not likely efficient or sustainable for the larger-scale implementation of this reactor in an ISRU context. Certainly, this reactor will need to be further developed as a two-chambered, parallel flow-through system, in which fresh microbial media and ferric oxides or other reducible minerals can be slowly brought into the reductive chamber, and the aqueous reduced metal waste can be disposed of. Similarly for the abiotic chamber, pure and anaerobic water will need to slowly enter the chamber, allowing the generated oxygen to be transported to an extraction system before the water can be recycled.

Figure 4:
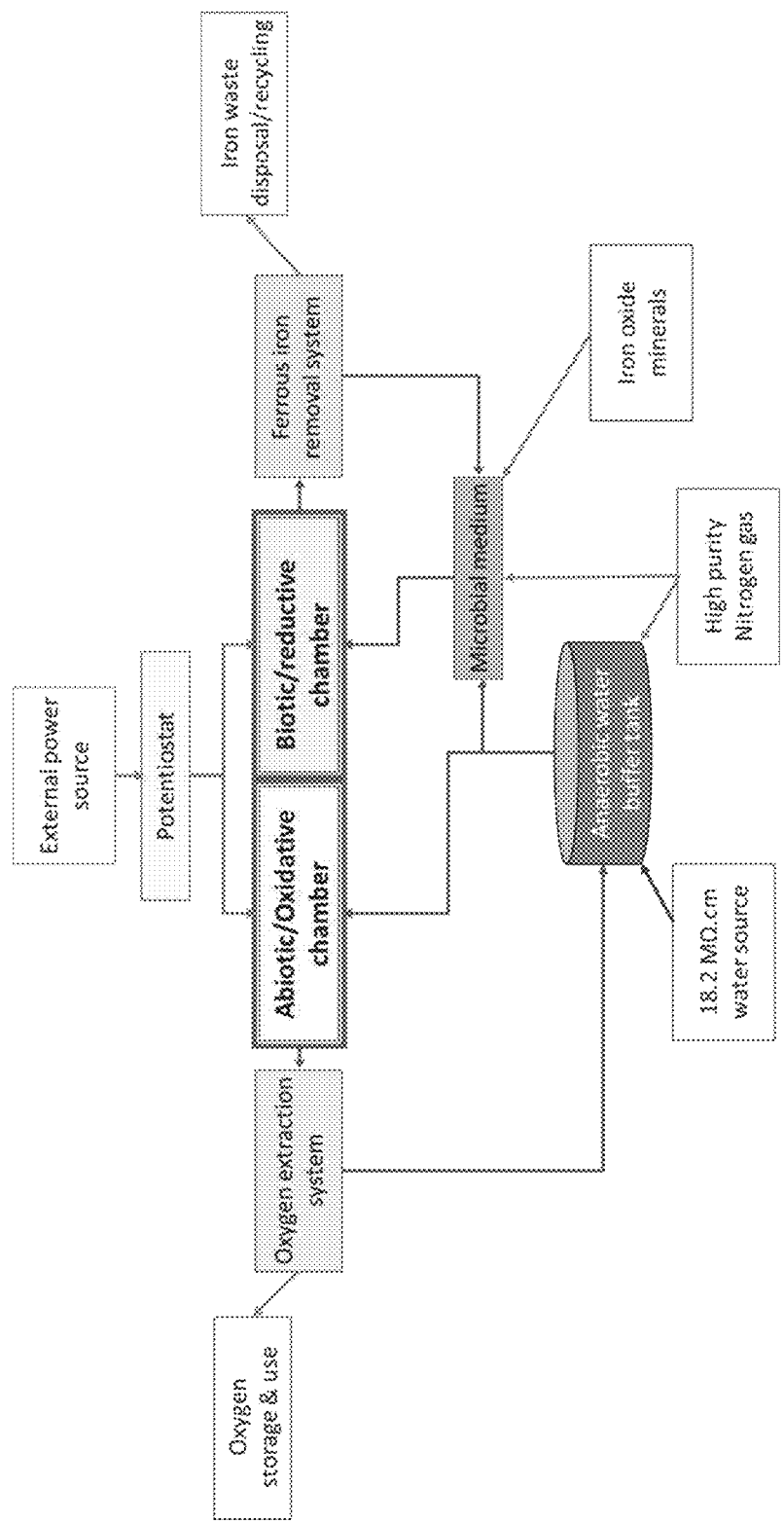
FIG. 4 illustrates an embodiment of an ISRU system comprising an oxygen-generating bioelectrical reactor.

A schematic of an embodiment of a comprehensive ISRU system is illustrated, for example, in FIG. 4, and discussed below. In general, the core bio-electrochemical reactor is highlighted in the center, with supporting systems such as water, nitrogen, electrical, as well as oxygen and waste products around the periphery and connected as shown.

Water System

While the bio-electrochemical reactor disclosed herein did not create any net water mass losses, it did lead to a transfer of water mass from the oxidative chamber to the reductive chamber. Therefore, a water management system could be employed to provide very clean and anaerobic water (i.e. nitrogen-purged 18.2 MΩ·cm water) to the reactor, as well as regulate the balance of water between both sides of the reactor through a buffer tank. Similarly, a separate tank holding microbial medium may be used to ensure the appropriate conditions (such as pH, nutrient concentrations, etc.) are maintained to sustain optimal microbial activity in the biotic chamber.

Nitrogen System

To ensure waters flowing into the reactor are perfectly anaerobic, a source of high purity gas (typically nitrogen, though other options such as argon could work just as well) could be used to purge waters of any potential oxygen they might carryover from their sources.

Electrical System

The bio-electrochemical reactor as disclosed and exemplified herein depended on an external energy source to produce the electric potential applied to the working electrode and sustain electrical current. Any standard voltage supply can suffice, such that the power source could depend on any power system established on a field location. Solar power could likely to prove valuable in that respect.

Ferric Oxide (or Other) Minerals

The consumable material which did get lost through the reaction of this system was ferric oxide minerals. Accordingly, these minerals could be extracted from local terrain and prepared as necessary (i.e., separated from other mineral phases, salts removed, etc.) before being injected into the system.

Outputs

The bio-electrochemical reactor presented here used electricity and ferric oxides as input, and produced ferrous iron and oxygen as outputs. As such, it could be necessary to continually remove ferrous iron from the biotic reductive chamber as it can become toxic to bacteria at high concentrations, as well as inhibit the core chemical reaction. This can be accomplished as part of a flow-through design, as water slowly flowing out of the biotic chamber can be processed to remove the ferrous iron. While the water can be recycled back as microbial growth medium, the iron would be disposed of, or recycled, as needed. On the other side of the equation, the flow-through design would cycle oxygen-generating water to an extraction process, separating out oxygen gas from water, after which the water will be reused as part of the water system.

Other Applications and Uses

The bioelectrical reactor disclosed herein was designed with at least an eye to oxygen-generating ISRU systems. However, this unique reactor has also the potential to serve other uses in research and environmental remediation, as follows:

Research Instrument for Exploring Microbial Respiration and Energetics

Previous and extensive research into the use of electroactive bacteria and fuel cells has typically depended on microbial anode reduction. The novelty of this system is that it successfully made use of the reversal of the Mtr biochemical pathway to promote cathode oxidation, thus driving an oxidizing fuel cell and catalyzing otherwise improbable geochemical reactions.

More typical anode-reducing reactors have already proven their use in academic and laboratory settings as a research instrument and an essential tool in isolating metabolic processes from their associated geochemical impact, as well as allowing the predictive quantification of energetics required in microbial respiration. This process could be studied against a wide range of metal oxide substrates commonly associated with *S. oneidensis* respiration in the reductive chamber, such as manganese oxide minerals. Thus, this new cathode-oxidizing reactor could serve the same purpose, but could instead be used to help study oxidative processes (such as water or metal oxidation, as described above), as well as their impact on geochemical and redox gradients on the environment. Last but equally important, this bioelectric reactor could be central in identifying new and yet undescribed microbial metabolic pathways such as, in this case, the reversal of Mtr respiration pathway, a process unheard-of until recently, and only validated through the development of cathode-oxidizing bioelectric reactors.

Applications in Environmental Remediation

Anode-reducing microbial fuel cells have been studied and characterized, and have been put to use in applications of environmental remediation, focusing on the oxidation of organic contaminants. New cathode-oxidizing reactors could thus also be used to process wastewater, with particular potential in treating redox-sensitive inorganic contaminants. Specifically, well-known, potentially toxic, inorganic substrates such as perchlorate or uranium could be reduced in the biotic/reductive chamber via well-known microbial respiratory pathways (i.e., perchlorate reductase), decreasing their environmental risks. At the same time, remediation of other contaminants could be performed in the abiotic/oxidative chamber of the system, decreasing toxicity through oxidation. Compounds such as hydrogen sulfide, arsenic, antimony or manganese could be oxidized, and even precipitated into mineral phases, thus removing them as a dissolved contaminant and as environmental risks.

Given the novelty of this cathode-oxidizing bioelectric reactor, such industrial applications could be explored. However, the positive results in catalyzing oxidative reactions presented here (both in producing oxygen, as well as precipitating ferric and manganese oxides, see section 4 above) serve as a proof-of-concept that this system can work as designed and might find application in environmental remediation. In this respect, it is worth highlighting the fact the more typical, anode-reducing microbial fuel cells, have already been deployed to remediate organic contaminants in an economically viable and sustainable way, as exemplified with successful businesses (e.g., Aquacycl™). Thus, a path for the application of such bioelectric reactors for industrial and commercial applications does exist and could be emulated.

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Any of the components may be coupled to each other via friction, snap, sleeves, brackets, clips or other means now known in the art or hereinafter developed. Additionally, any reference to without contact (or similar phrases) may also include reduced contact or minimal contact.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. An oxygen-generating bioelectrical reactor comprising:
a first abiotic oxidative chamber containing water;
a second biotic reductive chamber containing an aqueous mixture of dissimilatory metal(loid)-reducing microorganisms and a water-insoluble metal(loid) oxide or hydroxide capable of microbially-catalyzed reduction by the dissimilatory metal(loid)-reducing microorganisms;
a proton-selective membrane disposed between the first abiotic oxidative chamber and the second biotic reductive chamber providing a pathway for protons to move from the abiotic oxidative chamber to the biotic reductive chamber;
a counter electrode configured in the first abiotic oxidative chamber in contact with the water;
a working electrode and a reference electrode configured in the second biotic reductive chamber in contact with the aqueous mixture; and
a circuit electrically connecting the counter electrode, working electrode, and reference electrode such that the counter electrode is connected to the working electrode providing a pathway for electrons to move from the abiotic oxidative chamber to the biotic reductive chamber, wherein the circuit is configured to apply an electrical potential between the working electrode and the reference electrode.

2. The reactor of claim 1, wherein the water-insoluble metal(loid) oxide or hydroxide capable of microbially-catalyzed reduction by the dissimilatory metal(loid)-reducing microorganisms is characterized as comprising metal(loid) ions M(x), wherein M is Fe, Mn, Cr, Mo, V, As, Co, Au, Pd, or Hg, and x=VI, V, IV, III, or II.

3. The reactor of claim 1, wherein the dissimilatory metal(loid)-reducing microorganisms comprise *Shewanella* or facultative anaerobes.

4. The reactor of claim 1, wherein the dissimilatory metal(loid)-reducing microorganisms belong to a genus selected from the group consisting of *Clostridium, Aeromonas, Albidiferax, Shewanella*, Geobacter, Geothrix *fermentans*, Deferribacter, Rhondoferax, Desulfobulbus, or *Thermoanaerobacter*.

5. The reactor of claim 1, wherein the water-insoluble metal(loid) oxide or hydroxide comprises one of $Fe_2O_3$, $Fe(OH)_3$ or $MnO_2$.

6. The reactor of claim 1, wherein the circuit comprises a potentiostat.

7. The reactor of claim 1, further comprising an electron shuttle in the aqueous mixture of the biotic reductive chamber.

8. The reactor of claim 7, wherein the electron shuttle comprises at least one of FADH, menadione (1,2,3,4-tetrahydro-2-methyl-1,4-dioxo-2-naphthalene sulfonic acid), lawsone (2-hydroxy-1,4-naphthoquinone), AQ2S (anthraquinone-2-sulfonate), and AQDS (anthraquinone-2,6-di sulfonate).

9. The reactor of claim 1, wherein the potential applied between the working and reference electrodes is from about −300 mV to about −400 mV vs. SHE.

10. The reactor of claim 1, wherein the water-insoluble metal(loid) oxide or hydroxide comprises $Fe_2O_3$, and the dissimilatory metal(loid)-reducing microorganisms comprise a wildtype or mutant strain belonging to the genus *Shewanella*.

11. An oxygen-generating bioelectrical reactor comprising:
an oxidative chamber containing water;
a reductive chamber containing an aqueous mixture of dissimilatory metal(loid)-reducing microorganisms and a water-insoluble metal(loid) oxide or hydroxide capable of microbially-catalyzed reduction by the dissimilatory metal(loid)-reducing microorganisms;
a proton-selective membrane, disposed between the oxidative chamber and the reductive chamber, for providing a pathway for protons to move from the water in the oxidative chamber to the aqueous mixture in the reductive chamber;
a counter electrode coupled to the oxidative chamber and in contact with the water;
a working electrode coupled to the reductive chamber and in contact with the aqueous mixture;
a reference electrode coupled to the reductive chamber and in contact with the aqueous mixture; and
a circuit electrically connecting the counter electrode, the working electrode, and the reference electrode such that the counter electrode is connected to the working electrode to provide a pathway for electrons to move from the oxidative chamber to the reductive chamber, the circuit being configured to apply an electrical potential between the working electrode and the reference electrode.

12. The reactor of claim 11, wherein the water-insoluble metal(loid) oxide or hydroxide capable of microbially-catalyzed reduction by the dissimilatory metal(loid)-reducing microorganisms is characterized as comprising metal(loid) ions M(x), wherein M is Fe, Mn, Cr, Mo, V, As, Co, Au, Pd, or Hg, and x=VI, V, IV, III, or II.

13. The reactor of claim 11, wherein the dissimilatory metal(loid)-reducing microorganisms comprise *Shewanella* or facultative anaerobes.

14. The reactor of claim 11, wherein the dissimilatory metal(loid)-reducing microorganisms belong to a genus selected from the group consisting of *Clostridium, Aeromonas, Albidiferax, Shewanella*, Geobacter, Geothrix *fermentans*, Deferribacter, Rhondoferax, Desulfobulbus, or *Thermoanaerobacter*.

15. The reactor of claim 11, wherein the water-insoluble metal(loid) oxide or hydroxide comprises at least one of $Fe_2O_3$, $Fe(OH)_3$ or $MnO_2$.

16. The reactor of claim 11, wherein the circuit comprises a potentiostat.

17. The reactor of claim 11, further comprising an electron shuttle in the aqueous mixture of the reductive chamber.

18. The reactor of claim 17, wherein the electron shuttle comprises at least one of FADH, menadione (1,2,3,4-tetrahydro-2-methyl-1,4-dioxo-2-naphthalene sulfonic acid), lawsone (2-hydroxy-1,4-naphthoquinone), AQ2S (anthraquinone-2-sulfonate), or AQDS (anthraquinone-2, 6-di sulfonate).

19. The reactor of claim 11, wherein the potential applied between the working electrode and the reference electrode is from about −300 mV to about −400 mV vs. SHE.

20. The reactor of claim 11, wherein the water-insoluble metal(loid) oxide or hydroxide comprises $Fe_2O_3$, and the dissimilatory metal(loid)-reducing microorganisms comprise a wildtype or mutant strain belonging to the genus *Shewanella*.

* * * * *